US010865390B2

(12) United States Patent
Ni et al.

(10) Patent No.: US 10,865,390 B2
(45) Date of Patent: *Dec. 15, 2020

(54) ALCOHOL DEHYDROGENASE MUTANT AND APPLICATION THEREOF IN SYNTHESIS OF DIARYL CHIRAL ALCOHOLS

(71) Applicant: Jiangnan University, Wuxi (CN)

(72) Inventors: Ye Ni, Wuxi (CN); Jieyu Zhou, Wuxi (CN); Guochao Xu, Wuxi (CN); Yue Wang, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/521,636

(22) Filed: Jul. 25, 2019

(65) Prior Publication Data

US 2019/0345456 A1 Nov. 14, 2019

Related U.S. Application Data

(63) Continuation of application No. PCT/CN2018/094506, filed on Jul. 4, 2018.

(30) Foreign Application Priority Data

Feb. 12, 2018 (CN) .................. 2018 1 0146472.6

(51) Int. Cl.
*C12N 9/04* (2006.01)
*C12P 17/12* (2006.01)
*C12N 15/70* (2006.01)

(52) U.S. Cl.
CPC .......... *C12N 9/0006* (2013.01); *C12N 15/70* (2013.01); *C12P 17/12* (2013.01); *C12Y 101/01001* (2013.01)

(58) Field of Classification Search
None
See application file for complete search history.

(56) References Cited

U.S. PATENT DOCUMENTS

| 2019/0345455 | A1* | 11/2019 | Ni | .................. | C12N 9/0006 |
| 2019/0345456 | A1* | 11/2019 | Ni | .................. | C12N 9/0006 |
| 2019/0345457 | A1* | 11/2019 | Ni | .................. | C12P 17/12 |

FOREIGN PATENT DOCUMENTS

| CN | 102559520 A | 7/2012 |
| CN | 105936895 A * | 9/2016 |

(Continued)

OTHER PUBLICATIONS

PIR Accession No. F86228, published Mar. 2, 2001 (Year: 2001).*

(Continued)

*Primary Examiner* — Richard C Ekstrom
(74) *Attorney, Agent, or Firm* — IPro, PLLC

(57) ABSTRACT

The present disclosure discloses an alcohol dehydrogenase mutant and application thereof in synthesis of diaryl chiral alcohols, and belongs to the technical field of bioengineering. The alcohol dehydrogenase mutant of the present disclosure has excellent catalytic activity and stereoselectivity, and may efficiently catalyze the preparation of a series of chiral diaryl alcohols in R- and S-configurations. By coupling alcohol dehydrogenase of the present disclosure to glucose dehydrogenase or formate dehydrogenase, the synthesis of chiral diaryl alcohol intermediates of various antihistamines may be achieved. Compared with the prior art, a method for preparing diaryl chiral alcohols through asymmetric catalytic reduction using the alcohol dehydrogenase of the present disclosure has the advantages of simple and convenient operation, high substrate concentra- (Continued)

tion, complete reaction and high product purity, and has great industrial application prospects.

4 Claims, 2 Drawing Sheets

Specification includes a Sequence Listing.

(56) References Cited

FOREIGN PATENT DOCUMENTS

| CN | 105936895 A | 9/2016 |
|---|---|---|
| CN | 105936909 A | 9/2016 |
| CN | 106047985 A | 10/2016 |
| CN | 108384765 A | 8/2018 |

OTHER PUBLICATIONS

Geneseq Accession No. BDN64439, published Mar. 23, 2017 (Year: 2017).*
Geneseq Accession No. BDN64440, published Mar. 23, 2017 (Year: 2017).*
Geneseq Accession No. BDN64441, published Mar. 23, 2017 (Year: 2017).*
GenBank Accession No. XP_003683578.1, published Jun. 2, 2017 (Year: 2017).*
GenBank Accession No. 5ZED_A, published Jan. 3, 2019 (Year: 2019).*
GenBank Accession No. 5ZEC_A, published Jan. 3, 2019 (Year: 2019).*

* cited by examiner

ALCOHOL DEHYDROGENASE MUTANT AND APPLICATION THEREOF IN SYNTHESIS OF DIARYL CHIRAL ALCOHOLS

TECHNICAL FIELD

The present disclosure relates to an alcohol dehydrogenase mutant and application thereof in synthesis of diaryl chiral alcohols, and belongs to the technical field of bioengineering.

BACKGROUND

Chiral diaryl alcohol compounds are key chiral intermediates for the synthesis of numerous drugs and fine chemicals, where chiral (4-chlorophenyl)-(pyridin-2-yl)-methanol (CPMA) is a key chiral intermediate for the synthesis of an antihistamine drug betahistine. The synthesis of chiral CPMA by chemical asymmetric reduction using prochiral (4-chlorophenyl)-(pyridin-2-yl)-methanone (CPMK) as a raw material is mainly achieved by the following five techniques:

1. at a substrate concentration of 1.0 mM, using trans-$RuCl_2[(R)$-xylbinap][(R)-daipen] as a catalyst to react at room temperature for 24 h under the nitrogen pressure of 40-60 psi, so as to obtain (S)-(4-chlorophenyl)-(pyridin-2-yl)-methanol ((S)-CPMA) with an ee value of 60.6% and a yield of 98% through reduction. (C. Y. Chen, et al., *Org. Lett.*, 2003, 5, 5039-5042);

2. using (S)-[Ru(BINAP)$Cl_2]_2$($NE_3$) as a catalyst to obtain (S)-CPMA with an ee value of 99% through pressurization, hydrogenation and reduction (Zhao Zhiquan, et al., *Chinese Journal of Pharmaceuticals*, 2006, 37, 726-727);

3. using CPMK as a raw material and (S,S)-6-CHOONa as a catalyst to react at 50° C. and a substrate concentration of only 0.2 mM for 24 h, so as to obtain (R)-(4-chlorphenyl)-(pyridin-2-yl)-methanol ((R)-CPMA) with an ee value of 40.8% and a yield of 90% through reduction (B. G. Wang, *Org. Lett.*, 2017, 19, 2094-2097);

4. using CPMK as a raw material for three-step reaction, (1) first protecting with trifluoromethanesulfonic anhydride and the like, (2) using a catalyst palladium ligand, Me-CBS and the like to reduce a carbonyl group to an S configuration hydroxyl group, and (3) performing deprotection by triphenylphosphine palladium, so as to obtain (S)-CPMA (Chinese patent CN101848893A); and 5. using chiral BINAL-H as a chiral reducing agent for oriented synthesis of a single configuration of CPMA at a substrate concentration of 400 mM CMPK, where after recrystallization of ethyl acetate-petroleum ether, the yield of (R)-CPMA is 88.2%, the purity is 96.2%, the yield of (S)-CPMA is 87.4%, and the purity is 95.7% (Chinese patent CN103121966A).

It can be seen that the above reactions have the problems of high cost of the noble metal ligand catalysts, low substrate concentration, high pressure conditions for the reactions, many operation steps, and low optical purity of the materials, which cannot meet the requirements of drugs on the optical purity, and is not favorable for industrial production.

Biocatalysis refers to a process of chemical conversion using enzymes or biological organisms (cells, organelles, tissues, etc.) as a catalyst under mild action conditions, which is completed in an environment of normal temperature, a neutral environment, water or the like, and has unique advantages for the synthesis of chiral active pharmaceutical ingredients. It meets the goals of industrial development such as "sustainable development", "green chemistry" and "environmentally benign manufacturing". Compared with chemical synthesis methods, the use of alcohol dehydrogenase to asymmetrically reduce the carbonyl group in prochiral ketone has the advantages of high stereoselectivity, mild reaction conditions and the like, and has important economic and social values and ecological significance. The biological asymmetric reduction method may be realized mainly by the following four techniques:

1. in 2007, after Truppo et al. screened a series of commercial ketoreductases KRED, it was found that although some ketoreductases had a reducing ability to diaryl substrates, the stereoselectivity was just ordinary, a substrate spectrum was narrow, and substituent groups in the substrates had a great impact on the stereoselectivity; and only KRED124 may asymmetrically reduce CPMK to generate (R)-CPMA, the ee value was 94%, the conversion rate was 98%, and the addition of glucose dehydrogenase was required to achieve coenzyme circulation (M. D. Truppo, *Org. Lett.*, 2007, 9, 335-338);

2. in 2009, Zhu Dunming et al. discovered that a recombinant carbonyl reductase SsCR derived from *Sporobolomyces salmonicolor* and mutants thereof may stereoselectively reduce different diaryl ketone substrates (8-99% ee), with the aid of glucose dehydrogenase, (R)-CPMA was generated by reducing CPMK, the conversion rate was 62%, and the enantioselectivity was 88% (R) (D. M. Zhu, *Org. Lett.*, 2008, 10, 525-528);

3. in 2012, Zhou Jieyu et al. screened a *Kluyveromyces* sp. CCTCCM2011385 by traditional enrichment culture, which may catalyze the reduction of CPMK to generate (S)-CPMA (87% ee), however, due to the low content of active enzyme in wild fungi, only a 2 g/L substrate may be catalyzed at most, the product concentration is low, and the separation cost is high, so it cannot meet application needs, (Y. Ni, *Process Biochem.*, 2012, 47, 1042-1048; Chinese patent CN102559520A); and 4. in 2013, Li Zhe et al. studied the asymmetric reduction to a series of diaryl ketones by a carbonyl reductase PasCR derived from *Pichia pastoris* GS115, the substrate concentration was 10 mM, and the conversion rate was only 50% at most (LiZhe et al., *Chinese Journal of Biotechnology*, 2013, 29, 68-77).

It can be seen that the stereoselectivity for preparing chiral CPMA by the biological asymmetric reduction method can hardly meet the pharmaceutical requirement for an enantiomeric excess of more than 95%, and in particular, a reductase for synthesizing and preparing (S)-CPMA is unavailable, so there is an urgent need to develop a highly efficient and highly stereoselective bioenzyme catalyst.

SUMMARY

In view of the problem of low stereoselectivity of alcohol dehydrogenase in the prior art, the present disclosure provides a series of alcohol dehydrogenase mutant proteins, a nucleic acid sequence encoding the mutant proteins, a recombinant expression vector and a recombinant expression transformant containing the nucleic acid sequence, and application of the alcohol dehydrogenase mutant proteins or the recombinant transformant expressing the alcohol dehydrogenase mutant proteins as a catalyst in asymmetric reduction and preparation of an optical chiral diaryl alcohol.

The present disclosure provides an alcohol dehydrogenase mutant with higher reactivity and stereoselectivity.

In an embodiment of the present disclosure, the amino acid sequence of the mutant includes an amino acid sequence obtained by mutation of one or more sites of amino acid glutamine at position 136, amino acid phenylalanine at position 161, amino acid serine at position 196, amino acid glutamic acid at position 214, amino acid threonine at position 215 and amino acid serine at position 237 in the amino acid sequence shown in SEQ ID No. 2.

In an embodiment of the present disclosure, the mutant includes the substitution of glycine for glutamic acid at position 214 of the alcohol dehydrogenase with the amino acid sequence shown in SEQ ID No. 2, which is named M1.

In an embodiment of the present disclosure, the mutant includes the substitution of valine for glutamic acid at position 214 of the alcohol dehydrogenase with the amino acid sequence shown in SEQ ID No. 2, which is named M2.

In an embodiment of the present disclosure, the mutant includes the substitution of glycine for glutamic acid at position 214 of the alcohol dehydrogenase with the amino acid sequence shown in SEQ ID No. 2, and the substitution of cysteine for serine at position 237, which is named M3.

In an embodiment of the present disclosure, the mutant includes the substitution of glycine for glutamic acid at position 214 of the amino acid sequence shown in SEQ ID No. 2, the substitution of cysteine for serine at position 237, and the substitution of asparaginate for glutamine at position 136, which is named M4.

In an embodiment of the present disclosure, the mutant includes the substitution of glycine for glutamic acid at position 214 of the amino acid sequence shown in SEQ ID No. 2, the substitution of cysteine for serine at position 237, the substitution of asparaginate for glutamine at position 136, and the substitution of glycine for serine at position 196, which is named M5.

In an embodiment of the present disclosure, the mutant includes the substitution of glycine for glutamic acid at position 214 of the amino acid sequence shown in SEQ ID No. 2, the substitution of cysteine for serine at position 237, the substitution of asparaginate for glutamine at position 136, the substitution of glycine for serine at position 196, and the substitution of valine for phenylalanine at position 161, which is named M6.

In an embodiment of the present disclosure, the mutant includes the substitution of valine for glutamic acid at position 214 of the amino acid sequence shown in SEQ ID No. 2, and the substitution of serine for threonine at position 215, which is named M7.

In an embodiment of the present disclosure, the mutant includes the substitution of asparaginate for glutamine at position 136 of alcohol dehydrogenase with an amino acid sequence shown in SEQ ID No. 1, and the substitution of valine for phenylalanine at position 161, which is named M8.

In an embodiment of the present disclosure, the mutant includes the substitution of glycine for serine at position 196 of the alcohol dehydrogenase with the amino acid sequence shown in SEQ ID No. 1, and the substitution of cysteine for serine at position 237, which is named M9.

In an embodiment of the present disclosure, a recombinant strain expressing the mutant is provided.

In an embodiment of the present disclosure, a method for constructing the recombinant strain includes the following steps: cloning a nucleotide molecule encoding the mutant into a recombinant vector, transforming the resulting recombinant vector into a transformant to obtain a recombinant expression transformant, and culturing the resulting recombinant expression transformant and conducting isolation and purification to obtain the mutant.

In an embodiment of the present disclosure, the host of the recombinant strain is *Escherichia coli* and plasmid is pET28a (+).

In an embodiment of the present disclosure, the host of the recombinant strain is *E. coli* BL21 (DE3).

The present disclosure also provides a method for producing an alcohol dehydrogenase by using the recombinant strain, specifically including the following steps: inoculating the recombinant strain into an LB medium containing 40-60 μg/mL kanamycin sulfate for shake cultivation at 30-40° C. and 100-200 rpm, adding 0.05-1.0 mM isopropyl-β-D-thiogalactofuranoside (IPTG) for induction at an inducing temperature of 16-30° C. when the absorbance $OD_{600}$ of a medium solution reaches 0.5-1.0, and inducing for 5-10 h to obtain the mutant for efficient expression of a recombinant alcohol dehydrogenase.

In an embodiment of the present disclosure, application of the mutant as a catalyst in the preparation of an optical pure chiral diaryl alcohol by asymmetric reduction of a prochiral carbonyl compound is provided.

In an embodiment of the present disclosure, the prochiral carbonyl compound is (4-chlorophenyl)-(pyridin-2-yl)-methanone, phenyl-(pyridin-2-yl)-methanone, (4-chlorophenyl)-(phenyl)-methanone, (4-fluorophenyl-(phenyl)-methanone, (4-bromophenyl)-(phenyl)-methanone, (4-methoxyphenyl)-(phenyl)-methanone, acetophenone, 4-chloroacetophenone or 4-chlorobenzoyl chloride.

A method for producing chiral CPMA using an alcohol dehydrogenase specifically includes the following steps: constructing a reaction system, where CPMK concentration is 10-500 mM, the amount of the dehydrogenase mutant according to any one of claims 1-3 is 1-10 kU/L, and the amount of NADP+ is 0.1-1.0 mM; adding a coenzyme circulation system, wherein the coenzyme circulation system contains glucose dehydrogenase GDH and D-glucose, the amount of glucose dehydrogenase GDH is 1-10 kU/L, the amount of D-glucose dosage is 20-1000 mM, and the concentration of a phosphate buffer is 0.1-0.2 M; performing reaction at 30-35° C. and pH 6-8 for 1-24 h; and extracting the chiral CPMA from a reaction solution according to an organic solvent extraction method after asymmetric reduction reaction.

In an embodiment of the present disclosure, the coenzyme circulation system may also be phosphite/phosphite dehydrogenase (FTDH), formic acid/formate dehydrogenase (FDH), lactic acid/lactate dehydrogenase (LDH) or glycerol/glycerol dehydrogenase.

In an embodiment of the present disclosure, the (R)- and (S)-CPMA is chromatographed by taking 100 μL reaction solution, adding 500 μL ethyl acetate, shaking for 1-2 min, centrifuging at 12,000 rpm for 2-5 min, placing a supernatant into a centrifuge tube, and after an organic phase is naturally volatilized completely, adding 500 μL chromatographic pure ethanol for chiral liquid chromatography of a conversion rate and an ee value. The specific chromatographic conditions are as follows: Daicel Chiralcel OB-H (5 μm, 250 mm×4.6 mm) liquid chromatography column, mobile phases are n-hexane: ethanol: ethanolamine (90:10: 0.01, v/v/v), the flow rate is 1 mL/min, the column temperature is 30° C., the UV detection wavelength is 254 nm, the injection volume is 10 μL, and the retention time for (R)-CPMA and that for (S)-CPMA are 11.14 min and 12.34 min respectively.

The present disclosure has the beneficial effects that:

(1) the alcohol dehydrogenase mutant obtained in the present disclosure has high activity to various carbonyl compounds, and may catalyze the reduction of a plurality of aliphatic or aryl-substituted ketone substrates, especially diaryl ketone substrates having a large steric hindrance, and molecular modification on KpADH is achieved through the combination of mutation means to increase the stereoselectivity of the enzyme, which will make it more industrially useful;

(2) compared with the wild type alcohol dehydrogenase KpADH, the alcohol dehydrogenase mutant M6 of the present disclosure has an inverted S-stereoselectivity for the substrate CPMK, the ee value of a product CPMA is reversed to 97.8% (S) from 82% (R) of the wild type, M7 has a higher R-stereoselectivity for the substrate CPMK, and the ee value of a product CPMA is increased to 99% (R) or above from 82% (R) of the wild type. The alcohol dehydrogenase mutant obtained in the present disclosure is particularly suitable for asymmetric reduction of diaryl ketones, and has good industrial application prospects.

DETAILED DESCRIPTION

Figure 1:
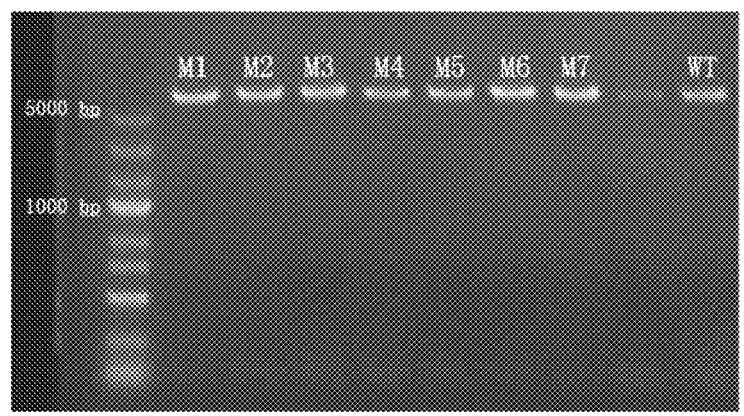
FIG. 1 is a whole plasmid PCR nucleic acid electropheretogram of wild type and alcohol dehydrogenase mutants M1 to M7.
Figure 2:
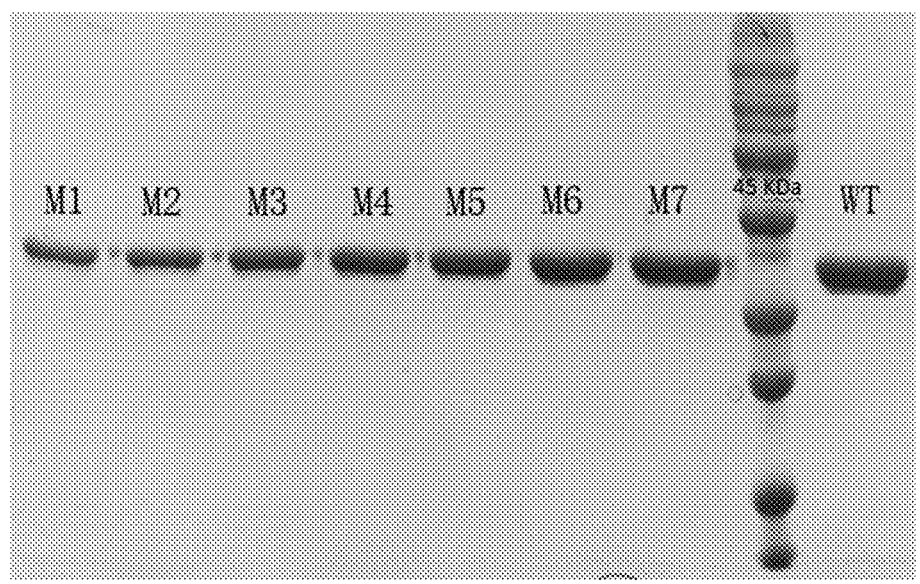
FIG. 2 is SDS-PAGE analysis of alcohol dehydrogenase mutants M1 to M7, respectively.
Figure 3:
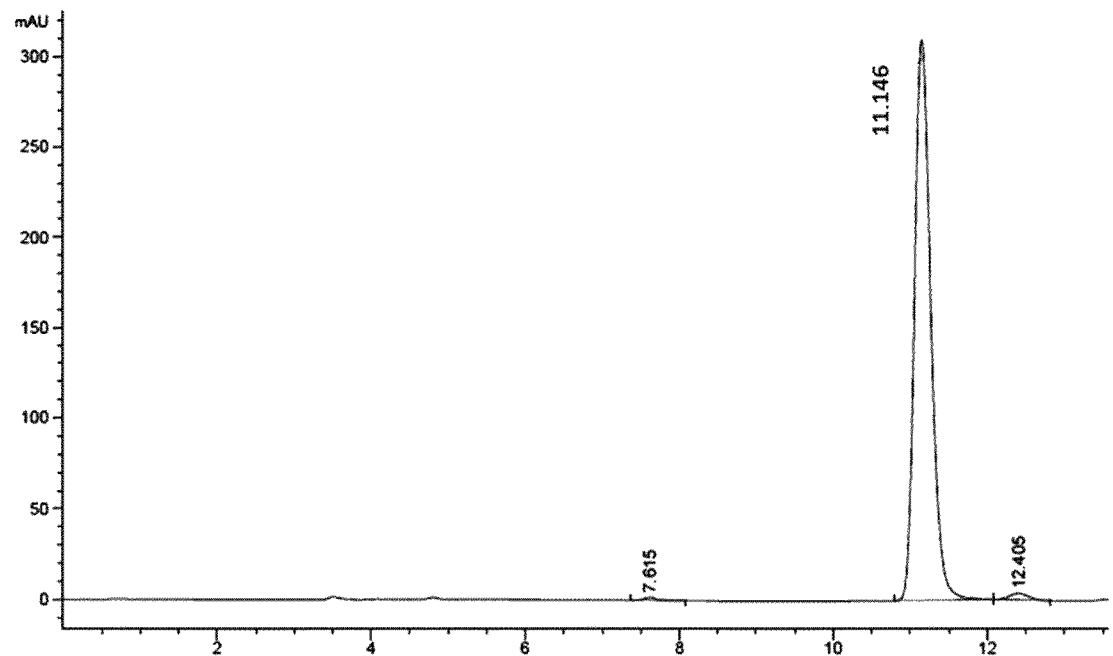
FIG. 3 is a chiral liquid chromatogram of a product produced from CPMK reduction catalyzed by an alcohol dehydrogenase mutant M6.
Figure 4:
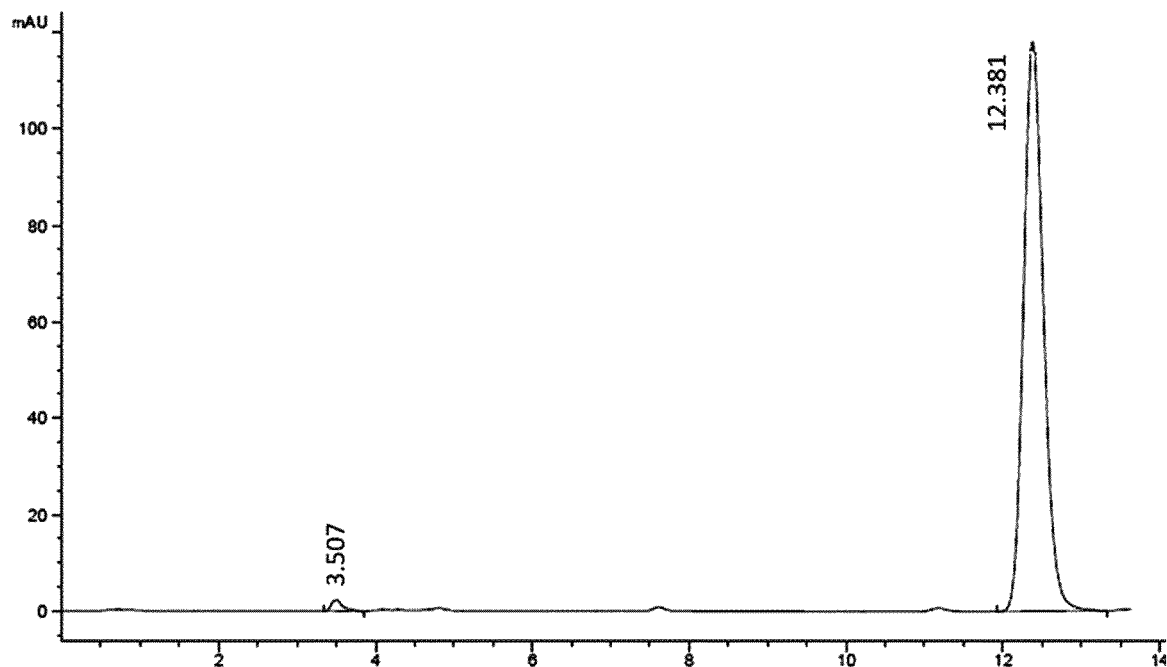
FIG. 4 is a chiral liquid chromatogram of a product produced from CPMK reduction catalyzed by an alcohol dehydrogenase mutant M7.

The present disclosure will be described in detail below by means of specific Examples, but this does not limit the present disclosure to the scope of the described Examples. The experimental methods without indicated specific experimental conditions in the following Examples may be selected according to conventional methods and conditions, or according to the specification.

Example 1: Method for Measuring Activity of Alcohol Dehydrogenase

Adopting a total reaction system of 200 μL including: 1.0 mM NADPH, 1.0 mM substrate CPMK and sodium phosphate buffer (PBS, 100 mM, pH 7.0), fully and evenly mixing, maintaining at 30° C. for 2 min, adding an appropriate amount of enzyme solution, and detecting the change in light absorption at 340 nm.

The enzyme activity was calculated by the following formula:

Enzyme activity $(U)=EW \times V \times 10^3/(6220 \times 1)$;

in the formula, EW is the change in absorbance at 340 nm in 1 min; V is the volume of a reaction solution in mL; 6220 is the molar extinction coefficient of NADPH in L/(mol·cm); and 1 is the optical path distance in cm. One activity unit (U) corresponds to the amount of enzyme required to catalyze the oxidation of 1 μmol NADPH per minute under the above conditions.

Method for determining optical purity ee:

$$ee = \frac{AS - AR}{AS + AR} \times 100\%;$$

$A_S$: molar concentration of (S)-CPMA obtained by liquid chromatography; and $A_R$: molar concentration of (R)-CPMA obtained by liquid chromatography.

Example 2: Construction of Alcohol Dehydrogenase Mutant Gene and Recombinant Expression Transformant A whole plasmid PCR method was used for site-directed mutagenesis on amino acid residues at positions 136, 161, 196, 214, 215 and 237 to construct an iterative combination mutant. The primer design was as follows (all described in the 5'-3' direction, and the underline represents the mutation site):

M1 (using pET28a-KpADH recombinant plasmid as a template):

```
E214G-F:
                             (SEQ ID NO. 3)
AAG AAACTA AAT GGTACT TGT;

E214G-R:
                             (SEQ ID NO. 4)
AAT TTCACA AGTACC ATT TAG;
```

M2 (using pET28a-KpADH recombinant plasmid as a template):

```
E214V-F:
                             (SEQ ID NO. 5)
AAG AAACTA AATGTTACT TGT;

E214V-R:
                             (SEQ ID NO. 6)
AAT TTCACA AGTAAC ATT TAG;
```

M3 (using M1 recombinant plasmid as a template):

```
S237C-F:
                             (SEQ ID NO. 7)
AAGACTCACTTCTGTCAATTC;

S237C-R:
                             (SEQ ID NO. 8)
ATCAATGAATTGACAGAAGTG;
```

M4 (using M3 recombinant plasmid as a template):

```
Q136N-F:
                             (SEQ ID NO. 9)
ACCCCACATAGAAATAATGAT;

Q136N-R:
                             (SEQ ID NO. 10)
AGTTGGATCATTATTTCTATG;
```

M5 (using M4 recombinant plasmid as a template):

```
S196G-F:
                             (SEQ ID NO. 11)
ACTATCCACCCAGGTTTCGTT;

S196G-R:
                             (SEQ ID NO. 12)
TCCGAAAACGAAACCTGGGTG;
```

M6 (using M5 recombinant plasmid as a template):

F161V-F:
(SEQ ID NO. 13)
TATGAAAATGTC<u>GTT</u>ACTGCT;

F161V-R:
(SEQ ID NO. 14)
ACAATAAGCAGT<u>AAC</u>GACATT;

M7 (using pET28a-KpADH recombinant plasmid as a template):

E214V/T215S-F:
(SEQ ID NO. 15)
AAGAAACTAAAT<u>GTTAGC</u>TGTGAA;

E214V/T215S-R:
(SEQ ID NO. 1+)
GATAATTTCACA<u>GCTAAC</u>ATTTAG;

M8 (using pET28a-KpADH$_{Q136N}$ recombinant plasmid as a template):

F161V-F:
(SEQ ID NO. 17)
TATGAAAATGTC<u>GTT</u>ACTGCT;

F161V-R:
(SEQ ID NO. 18)
ACAATAAGCAGT<u>AAC</u>GACATT;

M9 (using pET28a-KpADH$_{S196G}$ recombinant plasmid as a template):

S237C-F:
(SEQ ID NO. 19)
AAGACTCACTTC<u>TGT</u>CAATTC;

S237C-R:
(SEQ ID NO. 20)
ATCAATGAATTG<u>ACA</u>GAAGTG.

A PCR reaction system was: a PCR reaction system (50 µL) including KOD enzyme (2.5 U/mL) 1.0 µL, template (5-50 ng) 1.0 µL, dNTP 4.0 µL, 10× reaction buffer 5.0 µL, forward primer 1.0 µL, reverse primer 1.0 µL, and the rest of ddH2O to make the reaction system 50 µL in total.

A PCR amplification procedure was: (1) denaturation at 94° C. for 3 min, (2) denaturation at 94° C. for 30 sec, (3) annealing at 54° C. for 30 sec, (4) extension at 72° C. for 150 sec, repeating steps (2) to (4) for 10-15 cycles, finally extension at 72° C. for 10 min, and storing a PCR amplification product at 4° C.

After PCR, DpnI restriction enzyme was added into a reaction mixture and incubated at 37° C. for 1 h, 10 µL digested PCR reaction solution was transferred into 50 µL *E. coli* BL21 (DE3) competent cells through CaCl$_2$ thermal transformation, and the cells were used to uniformly coat an LB agar plate containing 50 µg/mL kanamycin sulfate for inversion culture at 37° C. for 12 h.

Example 3: Expression and Purification of Alcohol Dehydrogenase and Mutant Thereof Recombinant *Escherichia coli* carrying a stereoselective improvement mutant was inoculated into an LB medium containing kanamycin sulfate (50 µg/mL) at a transfer amount of 2% for shake cultivation at 37° C. and 200 rpm, 0.2 mM isopropyl-β-D-thiogalactofuranoside (IPTG) was added for induction at 25° C. when the absorbance OD$_{600}$ of the medium reached 0.8, after 8 hours of induction, a strain for efficient expression of a recombinant alcohol dehydrogenase mutant was obtained through 10 minutes of centrifugation at 8000 rpm, and the collected strain was suspended in a potassium phosphate buffer (100 mM, pH 6.0) for ultrasonication.

A column used for purification was a nickel affinity column HisTrap FF crude, and purification was achieved through affinity chromatography using a histidine tag on recombinant protein. The nickel column was equilibrated with a solution A first, a crude enzyme solution was loaded, a penetrating peak was further eluted off using the solution A, and after equilibrium, a solution B (20 mM sodium phosphate, 500 mM NaCl, and 1000 mM imidazole, pH 7.4) was used for gradient elution to elute off the recombinant protein bound to the nickel column, so as to obtain the recombinant alcohol dehydrogenase mutant. The purified protein was subjected to activity measurement (CPMK as substrate, and NADPH as coenzyme) and SDS-PAGE analysis. After purification of the nickel column, a single band was displayed at around 45 kDa, and the amount of impure protein was small, indicating that the column purification effect was good. The purified alcohol dehydrogenase protein was then replaced into a Tris-HCl (100 mM, pH 7.0) buffer using a Hi Trap Desalting column (GE Healthcare).

Example 4: Kinetic and Stereoselective Analysis of Alcohol Dehydrogenase Mutant

The activity of KpADH at different substrate concentrations and coenzyme concentrations was determined, and a double reciprocal curve was made based on the reciprocal of activity and substrate concentration to calculate kinetic parameters.

It can be seen from Table 1 that the $k_{cat}/K_m$ of KpADH to CPMK was 28.9 s$^{-1}$·mM$^{-1}$, the reduction product configuration was R configuration, and the ee value was 82.5%. The stereoselectivity of (R)-CPMA synthesized by mutants M2 and M7 was increased, and the ee values of the products were 92.3% and 99.1% respectively. Mutant M1 showed a reduced stereoselectivity, the reduction product configuration was also R configuration, and the ee value of the product was 3.29%. Mutants M3, M4, M5 and M6 showed an inverted stereoselectivity, the reduction products were in the S configuration, and the ee values of the products were 51.8%, 88.0%, 93.5% and 97.8% respectively. The reduction products of the control examples M8 and M9 were in the R configuration, the ee values of the products were little different from that of the wild type KpADH, and the mutation had no effect on the stereoselectivity of the enzyme.

TABLE 1

Kinetic parameters and stereoselectivity of alcohol dehydrogenase mutant

| Enzyme | Km (mM) | Vmax (μmol·min⁻¹·mg⁻¹) | Kcat (s⁻¹) | Kcat/Km (s⁻¹·mM⁻¹) | ee (%) | Config. (R/S) |
|---|---|---|---|---|---|---|
| KpADH | 0.410 | 17.9 | 11.8 | 28.9 | 82.5 | R |
| M1 | 0.52 | 11.1 | 7.32 | 14.1 | 3.29 | R |
| M2 | 0.574 | 17.5 | 11.7 | 14.2 | 92.3 | R |
| M3 | 0.632 | 9.32 | 6.16 | 9.74 | 51.8 | S |
| M4 | 0.861 | 10.2 | 6.76 | 7.85 | 88.0 | S |
| M5 | 0.72 | 21.3 | 17.0 | 23.6 | 93.5 | S |
| M6 | 1.12 | 25.2 | 20.1 | 17.9 | 99.8 | S |
| M7 | 0.702 | 21.3 | 14.2 | 20.3 | 99.9 | R |
| M8 (control example) | 0.604 | 22.3 | 14.8 | 24.6 | 83.5 | R |
| M9 (control example) | 0.730 | 26.5 | 17.6 | 24.1 | 81.7 | R |

Example 5: Substrate Specificity Analysis of Alcohol Dehydrogenase Mutant

The reduction on prochiral carbonyl compounds by the alcohol dehydrogenase mutants obtained in Example 2 was studied, and the studied prochiral carbonyl compounds include (4-chlorophenyl)-(pyridin-2-yl)-methanone (CPMK), phenyl-(pyridin-2-yl)-methanone, (4-chlorophenyl)-(phenyl)-methanone, (4-bromophenyl)-(phenyl)-methanone, (4-fluorophenyl)-(pyridin-2-yl)-methanone, (4-methoxyphenyl)-(phenyl)-methanone, acetophenone, 4-chloroacetophenone and 2-(4-chlorophenyl)acetyl chloride.

TABLE 2

Substrate specificity of alcohol dehydrogenase mutant

| Substrate | WT | M1 | M2 | M3 | M4 | M5 | M6 | M7 | M8 (control) | M9 (control) |
|---|---|---|---|---|---|---|---|---|---|---|
| (4-chlorophenyl)-(pyridin-2-yl)-methanone | 81.9 (R) | 24.2 (R) | 92.3 (R) | 65.4 (S) | 80.6 (S) | 87.7 (S) | 99.8 (S) | 99.9 (R) | 83.5 (R) | 81.7 (R) |
| phenyl-(pyridin-2-yl)-methanone | 26.3 (R) | 41.0 (R) | 30.6 (R) | 36.5 (R) | 20.7 (R) | 15.5 (R) | 6.81 (S) | 11.9 (R) | 22.3 (R) | 42.3 (R) |
| (4-chlorophenyl)-(phenyl)-methanone | 71.4 (S) | 63.2 (S) | 87.9 (S) | 33.2 (R) | 38.6 (R) | 62.0 (R) | 91.7 (R) | 99.4 (S) | 52.4 (S) | 78.4 (S) |
| (4-bromophenyl)-(phenyl)-methanone | 69.2 (S) | 49.3 (S) | 95.5 (S) | 63.3 (R) | 66.5 (R) | 70.9 (R) | 95.1 (R) | 99.6 (S) | 70.2 (S) | 59.2 (S) |
| (4-fluorophenyl)-(phenyl)-methanone | 25.3 (R) | 7.51 (R) | 0.56 (S) | 45.6 (R) | 49.1 (R) | 59.5 (R) | 64.2 (S) | 9.22 (R) | 55.3 (R) | 67.3 (R) |

TABLE 2-continued

Substrate specificity of alcohol dehydrogenase mutant

| Substrate | WT | M1 | M2 | M3 | M4 | M5 | M6 | M7 | M8 (control) | M9 (control) |
|---|---|---|---|---|---|---|---|---|---|---|
| 4-methoxy-(phenyl)-methanone (H₃CO-C₆H₄-CO-C₆H₅) | 14.9 (R) | 42.7 (R) | 23.2 (R) | 80.6 (R) | 82.6 (R) | 81.7 (R) | 95.1 (R) | 45.7 (S) | 24.5 (R) | 49.1 (R) |
| acetophenone | 59.2 (R) | 68.5 (R) | 45.3 (R) | 95.3 (R) | 91.5 (R) | 95.6 (R) | 95.3 (R) | 51.3 (R) | 66.2 (R) | 49.7 (R) |
| 4'-chloroacetophenone | 67.1 (R) | 86.3 (R) | 94.9 (R) | 88.9 (R) | 57.7 (R) | 49.1 (R) | 82.1 (R) | 95.1 (R) | 77.1 (R) | 47.3 (R) |
| 2-(4-chlorophenyl)acetyl chloride | 77.8 (R) | 94.5 (R) | 91.2 (S) | 99.8 (R) | 99.3 (R) | 99.9 (R) | 99.9 (R) | 77.5 (R) | 57.2 (R) | 42.8 (R) |

As can be seen from Table 2, compared with WT, the combined mutant M6 obtained by iterative combination mutation had an inverse stereoselectivity for (4-chlorophenyl)-(pyridin-2-yl)-methanone (CPMK), 4-bromophenyl-(pyridin-2-yl)-methanone and 4-methoxy-(phenyl)-methanone, and the ee values of products were all 95% or above; the mutant M6 had the same stereoselectivity as the wild type for 2-(4-chlorophenyl)acetyl chloride, and the ee values of products were all 99% or above; and the mutant M7 had the same stereoselectivity as WT for (4-chlorophenyl)-(pyridin-2-yl)-methanone (CPMK), and (4-bromophenyl)-(phenyl)-methanone, and the ee values of products were over 99%. Experiments have shown that the combination mutant strains obtained through iterative combination mutation had high R- and S-stereoselectivity for aryl ketone, especially large sterically hindered diaryl ketone substrates, and may be used as biocatalysts for preparation of R- and S-configuration chiral aryl alcohol intermediates.

Example 6: Preparation of (S)-CPMA and (R)-CPMA Through Asymmetric Reduction of CPMK by Alcohol Dehydrogenase Mutant A 20 mL biocatalytic system was established: 100 mM potassium phosphate buffer (pH 7.0), and the alcohol dehydrogenase mutants M6 and M7 obtained in Example 2 as well as wild KpADH 10 g/L, CPMK 100 mM, 200 mM and 500 mM were added (substrate added in batches). The reaction was performed at 30° C. and 200 rpm for 12 h with a constant pH of 7.5.

The conversion rate analysis results during the reaction are shown in Table 3, Table 4 and Table 5. It can be seen that both the wild type dehydrogenase and the mutants M6 and M7 may asymmetrically reduce 100 mM and 200 mM CPMK. When the CPMK concentration was 200 mM, the wild type KpADH and the two mutants (M6 and M7) required 12 h and 24 h respectively to achieve a conversion rate close to 99.9%. The final reduction product of the wild type KpADH was (R)-CPMA, and the ee value was 82%; the final reduction product of the mutant M6 was (S)-CPMA, and the ee value was 99.5%; and the final reduction product of the mutant M7 was (R)-CPMA, and the ee value was 99.7%. The obtained crude products of (R)-CPMA and (S)-CPMA were redissolved in ethanol, and corresponding pure products of (R)-CPMA and (S)-CPMA were added as seed crystals to recrystallize at 4° C. to finally obtain products with optical purity greater than 99.9% ee.

TABLE 3

Asymmetric reduction of CPMK catalyzed by wild type alcohol dehydrogenase KpADH

| Reaction time (h) | Conversion rate (%) | | |
|---|---|---|---|
| | 100 mM | 200 mM | 500 mM |
| 1 | 47.76 | 25.6 | 11.7 |
| 2 | 77.9 | 36.9 | 20.1 |
| 3 | 87.1 | 50.5 | 44.8 |
| 4 | 96.5 | 62.8 | 59.6 |
| 6 | 98.7 | 85.3 | 80.2 |
| 8 | 99.6 | 97.4 | 93.2 |
| 12 | >99.9 | 99.4 | 95.6 |
| 24 | >99.9 | 99.7 | 99.2 |

TABLE 4

Asymmetric reduction of CPMK catalyzed by alcohol dehydrogenase mutant M6

| Reaction time (h) | Conversion rate (%) | | |
|---|---|---|---|
| | 100 mM | 200 mM | 500 mM |
| 1 | 24.6 | 19.1 | 12.8 |
| 2 | 54.6 | 36.4 | 22.1 |
| 3 | 69.4 | 52.8 | 30.6 |
| 4 | 80.2 | 70.6 | 65.3 |
| 6 | 95.2 | 89.7 | 77.9 |
| 8 | 97.2 | 92.2 | 87.6 |
| 12 | 98.2 | 95.4 | 90.2 |
| 24 | 99.6 | 99.2 | 99.5 |

TABLE 5

Asymmetric reduction of CPMK catalyzed by alcohol dehydrogenase mutant M7

| Reaction time (h) | Conversion rate (%) | | |
|---|---|---|---|
| | 100 mM | 200 mM | 500 mM |
| 1 | 34.0 | 20.9 | 10.8 |
| 2 | 40.8 | 33.1 | 21.1 |
| 3 | 41.5 | 48.1 | 38.7 |
| 4 | 46.5 | 55.2 | 43.2 |
| 6 | 58.7 | 77.4 | 62.1 |
| 8 | 69.0 | 86.3 | 70.7 |
| 12 | 99.7 | 92.2 | 89.9 |
| 24 | 99.7 | 99.7 | 99.4 |

From this, it is understood that the alcohol dehydrogenase mutant enzymes M6 and M7 of the present disclosure have very good performance in terms of efficient, highly stereoselective asymmetric reduction of CPMK.

What is claimed is:

1. An alcohol dehydrogenase mutant, wherein the alcohol dehydrogenase mutant comprises an amino acid sequence having all of SEQ ID NO:2 except for:
   (a) a substitution of glycine for glutamic acid at position 214 of SEQ ID NO:2;
   (b) a substitution of glycine for glutamic acid at position 214 and a substitution of cysteine for serine at position 237 of SEQ ID NO:2;
   (c) a substitution of glycine for glutamic acid at position 214, a substitution of cysteine for serine at position 237, and a substitution of asparagine for glutamine at position 136 of SEQ ID NO:2;
   (d) a substitution of glycine for glutamic acid at position 214, a substitution of cysteine for serine at position 237, a substitution of asparagine for glutamine at position 136, and a substitution of glycine for serine at position 196 of SEQ ID NO:2;
   (e) a substitution of glycine for glutamic acid at position 214, a substitution of cysteine for serine at position 237, a substitution of asparaginate asparagine for glutamine at position 136, a substitution of glycine for serine at position 196, and a substitution of valine for phenylalanine at position 161 of SEQ ID NO:2; or
   (f) a substitution of valine for glutamic acid at position 214, and a substitution of serine for threonine at position 215 of SEQ ID NO:2, and wherein the alcohol dehydrogenase mutant has alcohol dehydrogenase activity.

2. An alcohol dehydrogenase mutant, wherein an amino acid sequence of the alcohol dehydrogenase mutant comprises all of SEQ ID NO:2, except for:
   (a) mutation of amino acid glutamine to asparagine at position 136,
   (b) mutation of amino acid phenylalanine to valine at position 161,
   (c) substitution of amino acid serine at position 196 with glycine,
   (d) substitution of amino acid glutamic acid at position 214 with glycine,
   (e) mutation of amino acid threonine to serine at position 215, or
   (f) substitution of amino acid serine at position 237 with cysteine, and wherein the alcohol dehydrogenase mutant has alcohol dehydrogenase activity.

3. A method for producing chiral (4-chlorophenyl)-(pyridin-2-yl)-methanol (CPMA) which comprises:

combining the alcohol dehydrogenase mutant of claim 1 at a concentration of 1 to 10 kU/L with prochiral (4-chlorophenyl)-(pyridin-2-yl)-methanone (CPMK) at a concentration of 10 to 500 mM, and NADP⁺ at a concentration of 0.1 to 1.0 mM;

adding a coenzyme circulation system comprising glucose dehydrogenase at a concentration of 1 to 10 kU/L, D-glucose at a concentration of 20 to 1000 mM, and a phosphate buffer;

incubating the coenzyme circulation system with the alcohol dehydrogenase mutant, CPMK, and NADP⁺ at 30 to 35° C. and a pH of 6 to 8 for 1 to 24 hours to produce CPMA; and extracting the CPMA by adding an organic solvent after an asymmetric reduction reaction;

wherein the coenzyme circulation system further comprises: (i) phosphite and phosphite dehydrogenase (FTDH), (ii) formic acid and formate dehydrogenase (FDH), (iii) lactic acid and lactate dehydrogenase (LDH), or (iv) glycerol and glycerol dehydrogenase.

4. A method for producing chiral (4-chlorophenyl)-(pyridin-2-yl)-methanol (CPMA), which comprises:

combining the alcohol dehydrogenase mutant of claim 2 at a concentration of 1 to 10 kU/L with prochiral (4-chlorophenyl)-(pyridin-2-yl)-methanone (CPMK) at a concentration of 10 to 500 mM, and NADP⁺ at a concentration of 0.1 to 1.0 mM;

adding a coenzyme circulation system comprising glucose dehydrogenase is at a concentration of 1 to 10 kU/L, D-glucose at a concentration of 20 to 1000 mM, and a phosphate buffer;

incubating the coenzyme circulation system with the alcohol dehydrogenase mutant, CPMK, and NADP⁺ at 30 to 35° C. and a pH of 6 to 8 for 1 to 24 hours to produce CPMA; and extracting the CPMA by adding an organic solvent after an asymmetric reduction reaction;

wherein the coenzyme circulation system further comprises: (i) phosphite and phosphite dehydrogenase (FTDH), (ii) formic acid and formate dehydrogenase (FDH), (iii) lactic acid and lactate dehydrogenase (LDH), or (iv) glycerol and glycerol dehydrogenase.

\* \* \* \* \*

SEQUENCE LISTING

<160> NUMBER OF SEQ ID NOS: 20

<210> SEQ ID NO 1
<211> LENGTH: 1029
<212> TYPE: DNA
<213> ORGANISM: Artificial Sequence
<220> FEATURE:
<223> OTHER INFORMATION: Synthetic DNA

<400> SEQUENCE: 1

```
atgagcgtat taattagtgg tgcttctgga tacattgcca acatatcgt cagagttctt      60 ttggaacaaa attacaaagt aattggtact gttagaagtc aagacaaagc tgataagtta     120 tgaaacaat ataataatcc taatttgtct tatgaaattg tacctgaaat agcaaactta      180
gatgcttttg atgacatttt taagaaacat ggtaaggaaa taaatatgt cattcatgca     240 gcttcaccag tgaacttcgg cgcaaaagat ttggaaaaag atttagttat tcctgccatt     300
aatggtacca agaatatgtt cgaagctatt aaaaagtatg ccccagatac tgtcgaacgt     360
gttgtaatga ctgcttctta tgcttcaatt atgaccccac atagacaaaa tgatccaact     420 ttaacttag atgaagaaac ttggaatcca gtaactgaag aaaatgctta tgaaaatgtc     480
ttcactgctt attgtgcttc aaaaactttt gctgaaaagg aagcttggaa gttcgttaaa     540
gaaaatagtg atgctgttaa gtttaaacta accactatcc acccatcctt cgttttcgga     600
cctcagaact tgatgaaga cgtcactaag aaactaaatg aaacttgtga aattatcaat     660
ggtttattac atgctccatt tgacaccaaa gtcgaaaaga ctcacttcag tcaattcatt     720
gatgttcgtg atgtcgccaa aactcacgtt ttgggtttcc aaaaagatga attaatcaac     780
caaagattgt tattatgtaa cggcgccttc tctcaacaag atattgttaa tgtatttaat     840
gaagatttcc cagagttaaa aggccaattc ccaccagaag ataaggacac cgatttaaac     900
aaaggtgtaa caggttgtaa aattgataat gaaaagacta aaaaattatt agcatttgaa     960
tttactcctt tccataaaac aattcatgac actgtctatc aaatttttaca taagaaggt   1020 agagtttaa                                                           1029
```

<210> SEQ ID NO 2
<211> LENGTH: 342
<212> TYPE: PRT
<213> ORGANISM: Artificial Sequence
<220> FEATURE:

<223> OTHER INFORMATION: Protein translated from synthetic DNA

<400> SEQUENCE: 2

| Met | Ser | Val | Leu | Ile | Ser | Gly | Ala | Ser | Gly | Tyr | Ile | Ala | Lys | His | Ile |
|---|---|---|---|---|---|---|---|---|---|---|---|---|---|---|---|
| 1 | | | | 5 | | | | | 10 | | | | | 15 | |

| Val | Arg | Val | Leu | Leu | Glu | Gln | Asn | Tyr | Lys | Val | Ile | Gly | Thr | Val | Arg |
|---|---|---|---|---|---|---|---|---|---|---|---|---|---|---|---|
| | | | 20 | | | | | 25 | | | | | 30 | | |

| Ser | Gln | Asp | Lys | Ala | Asp | Lys | Leu | Leu | Lys | Gln | Tyr | Asn | Asn | Pro | Asn |
|---|---|---|---|---|---|---|---|---|---|---|---|---|---|---|---|
| | | 35 | | | | | 40 | | | | | 45 | | | |

| Leu | Ser | Tyr | Glu | Ile | Val | Pro | Glu | Ile | Ala | Asn | Leu | Asp | Ala | Phe | Asp |
|---|---|---|---|---|---|---|---|---|---|---|---|---|---|---|---|
| | 50 | | | | | 55 | | | | | 60 | | | | |

| Asp | Ile | Phe | Lys | Lys | His | Gly | Lys | Glu | Ile | Lys | Tyr | Val | Ile | His | Ala |
|---|---|---|---|---|---|---|---|---|---|---|---|---|---|---|---|
| 65 | | | | | 70 | | | | | 75 | | | | | 80 |

| Ala | Ser | Pro | Val | Asn | Phe | Gly | Ala | Lys | Asp | Leu | Glu | Lys | Asp | Leu | Val |
|---|---|---|---|---|---|---|---|---|---|---|---|---|---|---|---|
| | | | | 85 | | | | | 90 | | | | | 95 | |

| Ile | Pro | Ala | Ile | Asn | Gly | Thr | Lys | Asn | Met | Phe | Glu | Ala | Ile | Lys | Lys |
|---|---|---|---|---|---|---|---|---|---|---|---|---|---|---|---|
| | | | 100 | | | | | 105 | | | | | 110 | | |

| Tyr | Ala | Pro | Asp | Thr | Val | Glu | Arg | Val | Val | Met | Thr | Ala | Ser | Tyr | Ala |
|---|---|---|---|---|---|---|---|---|---|---|---|---|---|---|---|
| | | 115 | | | | | 120 | | | | | 125 | | | |

| Ser | Ile | Met | Thr | Pro | His | Arg | Gln | Asn | Asp | Pro | Thr | Leu | Thr | Leu | Asp |
|---|---|---|---|---|---|---|---|---|---|---|---|---|---|---|---|
| | 130 | | | | | 135 | | | | | 140 | | | | |

| Glu | Glu | Thr | Trp | Asn | Pro | Val | Thr | Glu | Asn | Ala | Tyr | Glu | Asn | Val |
|---|---|---|---|---|---|---|---|---|---|---|---|---|---|---|
| 145 | | | | | 150 | | | | | 155 | | | | | 160 |

| Phe | Thr | Ala | Tyr | Cys | Ala | Ser | Lys | Thr | Phe | Ala | Glu | Lys | Glu | Ala | Trp |
|---|---|---|---|---|---|---|---|---|---|---|---|---|---|---|---|
| | | | | 165 | | | | | 170 | | | | | 175 | |

| Lys | Phe | Val | Lys | Glu | Asn | Ser | Asp | Ala | Val | Lys | Phe | Lys | Leu | Thr | Thr |
|---|---|---|---|---|---|---|---|---|---|---|---|---|---|---|---|
| | | | 180 | | | | | 185 | | | | | 190 | | |

| Ile | His | Pro | Ser | Phe | Val | Phe | Gly | Pro | Gln | Asn | Phe | Asp | Glu | Asp | Val |
|---|---|---|---|---|---|---|---|---|---|---|---|---|---|---|---|
| | | 195 | | | | | 200 | | | | | 205 | | | |

| Thr | Lys | Lys | Leu | Asn | Glu | Thr | Cys | Glu | Ile | Ile | Asn | Gly | Leu | Leu | His |
|---|---|---|---|---|---|---|---|---|---|---|---|---|---|---|---|
| | 210 | | | | | 215 | | | | | 220 | | | | |

| Ala | Pro | Phe | Asp | Thr | Lys | Val | Glu | Lys | Thr | His | Phe | Ser | Gln | Phe | Ile |
|---|---|---|---|---|---|---|---|---|---|---|---|---|---|---|---|
| 225 | | | | | 230 | | | | | 235 | | | | | 240 |

| Asp | Val | Arg | Asp | Val | Ala | Lys | Thr | His | Val | Leu | Gly | Phe | Gln | Lys | Asp |
|---|---|---|---|---|---|---|---|---|---|---|---|---|---|---|---|
| | | | | 245 | | | | | 250 | | | | | 255 | |

| Glu | Leu | Ile | Asn | Gln | Arg | Leu | Leu | Leu | Cys | Asn | Gly | Ala | Phe | Ser | Gln |
|---|---|---|---|---|---|---|---|---|---|---|---|---|---|---|---|
| | | | 260 | | | | | 265 | | | | | 270 | | |

| Gln | Asp | Ile | Val | Asn | Val | Phe | Asn | Glu | Asp | Phe | Pro | Glu | Leu | Lys | Gly |
|---|---|---|---|---|---|---|---|---|---|---|---|---|---|---|---|
| | | 275 | | | | | 280 | | | | | 285 | | | |

| Gln | Phe | Pro | Pro | Glu | Asp | Lys | Asp | Thr | Asp | Leu | Asn | Lys | Gly | Val | Thr |
|---|---|---|---|---|---|---|---|---|---|---|---|---|---|---|---|
| | 290 | | | | | 295 | | | | | 300 | | | | |

| Gly | Cys | Lys | Ile | Asp | Asn | Glu | Lys | Thr | Lys | Lys | Leu | Leu | Ala | Phe | Glu |
|---|---|---|---|---|---|---|---|---|---|---|---|---|---|---|---|
| 305 | | | | | 310 | | | | | 315 | | | | | 320 |

| Phe | Thr | Pro | Phe | His | Lys | Thr | Ile | His | Asp | Thr | Val | Tyr | Gln | Ile | Leu |
|---|---|---|---|---|---|---|---|---|---|---|---|---|---|---|---|
| | | | | 325 | | | | | 330 | | | | | 335 | |

| His | Lys | Glu | Gly | Arg | Val |
|---|---|---|---|---|---|
| | | | 340 | | |

<210> SEQ ID NO 3
<211> LENGTH: 21
<212> TYPE: DNA
<213> ORGANISM: Artificial Sequence
<220> FEATURE:
<223> OTHER INFORMATION: Synthetic DNA

<400> SEQUENCE: 3
aagaaactaa atggtacttg t                                   21

<210> SEQ ID NO 4
<211> LENGTH: 21
<212> TYPE: DNA
<213> ORGANISM: Artificial Sequence
<220> FEATURE:
<223> OTHER INFORMATION: Synthetic DNA

<400> SEQUENCE: 4
aatttcacaa gtaccattta g                                   21

<210> SEQ ID NO 5
<211> LENGTH: 21
<212> TYPE: DNA
<213> ORGANISM: Artificial Sequence
<220> FEATURE:
<223> OTHER INFORMATION: Synthetic DNA

<400> SEQUENCE: 5
aagaaactaa atgttacttg t                                   21

<210> SEQ ID NO 6
<211> LENGTH: 21
<212> TYPE: DNA
<213> ORGANISM: Artificial Sequence
<220> FEATURE:
<223> OTHER INFORMATION: Synthetic DNA

<400> SEQUENCE: 6
aatttcacaa gtaacattta g                                   21

<210> SEQ ID NO 7
<211> LENGTH: 21
<212> TYPE: DNA
<213> ORGANISM: Artificial Sequence
<220> FEATURE:
<223> OTHER INFORMATION: Synthetic DNA

<400> SEQUENCE: 7
aagactcact tctgtcaatt c                                   21

<210> SEQ ID NO 8
<211> LENGTH: 21
<212> TYPE: DNA
<213> ORGANISM: Artificial Sequence
<220> FEATURE:
<223> OTHER INFORMATION: Synthetic DNA

<400> SEQUENCE: 8
atcaatgaat tgacagaagt g                                   21

<210> SEQ ID NO 9
<211> LENGTH: 21
<212> TYPE: DNA
<213> ORGANISM: Artificial Sequence
<220> FEATURE:
<223> OTHER INFORMATION: Synthetic DNA

<400> SEQUENCE: 9
accccacata gaataatga t                                    21

<210> SEQ ID NO 10
<211> LENGTH: 21
<212> TYPE: DNA

```
<213> ORGANISM: Artificial Sequence
<220> FEATURE:
<223> OTHER INFORMATION: Synthetic DNA

<400> SEQUENCE: 10
agttggatca ttatttctat g                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic DNA

<400> SEQUENCE: 11
actatccacc caggtttcgt t                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic DNA

<400> SEQUENCE: 12
tccgaaaacg aaacctgggt g                                              21

<210> SEQ ID NO 13
<211> LENGTH: 21
<212> TYPE: DNA
<213> ORGANISM: Artificial Sequence
<220> FEATURE:
<223> OTHER INFORMATION: Synthetic DNA

<400> SEQUENCE: 13
tatgaaaatg tcgttactgc t                                              21

<210> SEQ ID NO 14
<211> LENGTH: 21
<212> TYPE: DNA
<213> ORGANISM: Artificial Sequence
<220> FEATURE:
<223> OTHER INFORMATION: Synthetic DNA

<400> SEQUENCE: 14
acaataagca gtaacgacat t                                              21

<210> SEQ ID NO 15
<211> LENGTH: 24
<212> TYPE: DNA
<213> ORGANISM: Artificial Sequence
<220> FEATURE:
<223> OTHER INFORMATION: Synthetic DNA

<400> SEQUENCE: 15
aagaaactaa atgttagctg tgaa                                           24

<210> SEQ ID NO 16
<211> LENGTH: 24
<212> TYPE: DNA
<213> ORGANISM: Artificial Sequence
<220> FEATURE:
<223> OTHER INFORMATION: Synthetic DNA

<400> SEQUENCE: 16
gataatttca cagctaacat ttag                                           24
```

```
<210> SEQ ID NO 17
<211> LENGTH: 21
<212> TYPE: DNA
<213> ORGANISM: Artificial Sequence
<220> FEATURE:
<223> OTHER INFORMATION: Synthetic DNA

<400> SEQUENCE: 17
tatgaaaatg tcgttactgc t                                          21

<210> SEQ ID NO 18
<211> LENGTH: 21
<212> TYPE: DNA
<213> ORGANISM: Artificial Sequence
<220> FEATURE:
<223> OTHER INFORMATION: Synthetic DNA

<400> SEQUENCE: 18
acaataagca gtaacgacat t                                          21

<210> SEQ ID NO 19
<211> LENGTH: 21
<212> TYPE: DNA
<213> ORGANISM: Artificial Sequence
<220> FEATURE:
<223> OTHER INFORMATION: Synthetic DNA

<400> SEQUENCE: 19
aagactcact tctgtcaatt c                                          21

<210> SEQ ID NO 20
<211> LENGTH: 21
<212> TYPE: DNA
<213> ORGANISM: Artificial Sequence
<220> FEATURE:
<223> OTHER INFORMATION: Synthetic DNA

<400> SEQUENCE: 20
atcaatgaat tgacagaagt g                                          21
```